(12) United States Patent
Shemmeri

(10) Patent No.: US 10,569,070 B1
(45) Date of Patent: Feb. 25, 2020

(54) MEDICATED PATCH APPLICATOR AND ASSOCIATED USE THEREOF

(71) Applicant: Nida Shemmeri, Horseheads, NY (US)

(72) Inventor: Nida Shemmeri, Horseheads, NY (US)

( * ) Notice: Subject to any disclaimer, the term of this patent is extended or adjusted under 35 U.S.C. 154(b) by 331 days.

(21) Appl. No.: 15/649,589

(22) Filed: Jul. 13, 2017

Related U.S. Application Data

(60) Provisional application No. 62/362,021, filed on Jul. 13, 2016.

(51) Int. Cl.
*A61M 35/00* (2006.01)
*B25G 1/06* (2006.01)
*B25G 1/10* (2006.01)
*A61K 9/70* (2006.01)
*A61M 25/02* (2006.01)

(52) U.S. Cl.
CPC ............ *A61M 35/003* (2013.01); *B25G 1/06* (2013.01); *B25G 1/102* (2013.01); *A61K 9/7038* (2013.01); *A61M 35/30* (2019.05); *A61M 2025/0266* (2013.01)

(58) Field of Classification Search
CPC .. A61M 35/00; A61M 35/005; A61M 35/006; A61M 35/30; A61M 2025/0266; B25G 1/01; B25G 1/02; B25G 1/04; B25G 1/06; B25G 1/066; B25G 3/02; B25G 3/04; B25G 3/06; B25G 3/12; B25G 3/38; B25G 3/32; B25G 3/34; B05C 17/0205; F16B 9/00; A61H 7/003; A61H 2205/081; A61K 9/7038; A61K 9/7084; A61K 9/7092; A61K 9/7023; A01M 3/022; A01M 3/04; A01M 7/0035; A01M 35/00; A61N 1/0484; A61N 1/0492; B25F 1/02; E01H 1/12; A45D 2200/1018; A45D 34/04
See application file for complete search history.

(56) References Cited

U.S. PATENT DOCUMENTS

| | | | | |
|---|---|---|---|---|
| 4,615,066 A | * | 10/1986 | Colognori | A47L 13/46 |
| | | | | 15/145 |
| 2006/0147256 A1 | * | 7/2006 | Richardson | B25G 1/06 |
| | | | | 403/91 |
| 2014/0128850 A1 | * | 5/2014 | Kerr | H01M 2/1022 |
| | | | | 606/1 |
| 2019/0038884 A1 | * | 2/2019 | Roux | A61M 35/00 |

* cited by examiner

*Primary Examiner* — Andrew J Mensh
*Assistant Examiner* — Martha G Rivas
(74) *Attorney, Agent, or Firm* — Ashkan Najafi

(57) ABSTRACT

A medicated patch applicator includes a portable handle having a centrally registered longitudinal axis, a flexible frame pivotally connected to the handle and selectively articulated relative thereto, and an implement adjustably coupled to a distal end of the handle and disposed at a proximal end of the frame. Such an implement is located adjacent to a juncture of the frame and the handle such that the implement linearly protrudes outwardly from the handle along the centrally registered longitudinal axis. Advantageously, the implement is capable of removing an existing back liner of an existing medicated patch during an application process of the existing medicated patch.

17 Claims, 8 Drawing Sheets

MEDICATED PATCH APPLICATOR AND ASSOCIATED USE THEREOF

CROSS REFERENCE TO RELATED APPLICATIONS

This is a non-provisional patent application that claims the benefit of U.S. provisional patent application No. 62/362,021 filed Jul. 13, 2016, which is incorporated by reference herein in its entirety.

STATEMENT REGARDING FEDERALLY SPONSORED RESEARCH OR DEVELOPMENT

Not Applicable.

REFERENCE TO A MICROFICHE APPENDIX

Not Applicable.

BACKGROUND

Technical Field

Exemplary embodiment(s) of the present disclosure relate to medicated patch applicators and, more particularly, to a manually operated, handheld device which enables an individual to easily apply an adhesive-backed, medicated patch to any area of his or her back. Ideal for consumers suffering back pain and living alone, the medicated patch applicator would permit its users to gain relief from pain, and do so without any assistance to apply the medicated patch.

Prior Art

At one time or another, approximately 80 percent of the populace—four out of every five consumers—will suffer a back injury, or a bout of back pain. And for many who suffer back pain, an over-the-counter, adhesive-backed patch— IcyHot® and Salonpas® being two of the most familiar brands—will bring relief: If, that is, they can get the patch onto the area of their back where it's needed. For those with a spouse, child, or parent in the household, the essential assistance may be close at hand—but for those living alone with back pain, applying the adhesive patch is practically impossible, meaning that the relief it would bring, for all intents and purposes, stays in the box. The invention to be presented and explored in the course of this report would correct this unfortunate situation, and permit the back-pain sufferer to apply the medicated patch to his or her own back.

Most back patches, however effective at alleviating pain or reducing swelling, are practically impossible to apply to one's own back; and to be able to do so, without exacerbating the back pain that made the patch necessary in the first place, would be a major improvement in the lives of people who experience back pain.

Accordingly, a need remains for a medicated patch applicator in order to overcome at least one aforementioned shortcoming. The exemplary embodiment(s) satisfy such a need by providing a manually operated, handheld device that is convenient and easy to use, lightweight yet durable in design, versatile in its applications, and designed for an individual to easily apply an adhesive-backed, medicated patch to any area of his or her back. Ideal for consumers suffering back pain and living alone, the medicated patch applicator would permit its users to gain relief from pain, and do so without any assistance to apply the medicated patch.

BRIEF SUMMARY OF NON-LIMITING EXEMPLARY EMBODIMENT(S) OF THE PRESENT DISCLOSURE

In view of the foregoing background, it is therefore an object of the non-limiting exemplary embodiment(s) to provide a medicated patch applicator for easily applying an adhesive-backed, medicated patch to any area of a user back. These and other objects, features, and advantages of the non-limiting exemplary embodiment(s) are provided by a medicated patch applicator including a portable handle having a centrally registered longitudinal axis, a flexible frame pivotally connected to the handle and selectively articulated relative thereto, and an implement adjustably coupled to a distal end of the handle and disposed at a proximal end of the frame. Such an implement is located adjacent to a juncture of the frame and the handle such that the implement linearly protrudes outwardly from the handle along the centrally registered longitudinal axis. Advantageously, the implement is capable of removing an existing back liner of an existing medicated patch during an application process of the existing medicated patch.

In a non-limiting exemplary embodiment, the frame includes a plurality of flexible struts each having a proximal end coupled to the distal end of the handle and extending outwardly therefrom. Such a flexible strut is angularly oriented away from the centrally registered longitudinal axis. A plurality of first fasteners are attached to the flexible struts, respectively. A plurality of support arms are attached to the first fasteners and engaged with the flexible struts and extending distally away therefrom, respectively. A plurality of second fasteners are attached to the support arms, respectively, and a roller having axially-offset opposed ends is rotatably engaged with the second fasteners, respectively.

In a non-limiting exemplary embodiment, the frame includes a substrate having a planar anterior surface and opposed lateral sides statically mated to the support arms, wherein the substrate is configured to receive the existing medicated patch along the planar anterior surface. A cover is pivotally connected to one of the support arms such the cover is articulated between open and closed positions relative to the substrate.

In a non-limiting exemplary embodiment, the frame has a substantially Y-shaped configuration.

In a non-limiting exemplary embodiment, the frame has a substantially yoke-shaped configuration.

In a non-limiting exemplary embodiment, the handle includes a first tubular section, a pivoting joint disposed at a distal end of the first tubular section, and a second tubular section engaged with the pivoting joint and selectively rotatable relative to the first tubular section.

In a non-limiting exemplary embodiment, the second tubular section includes an actuator operably coupled to the implement wherein the implement is displaced along a linear path parallel to the centrally registered longitudinal axis when the actuator is depressed.

In a non-limiting exemplary embodiment, the pivoting joint includes a ball and socket mechanism intercalated between the first tubular section and the second tubular section.

The present disclosure further includes a method of utilizing a medicated patch applicator for easily applying an adhesive-backed, medicated patch to any area of a user back.

Such a method includes the steps of: providing an existing medicated patch; providing a portable handle having a centrally registered longitudinal axis; providing and pivotally connecting a flexible frame to the handle such that the flexible frame is selectively articulated relative to the handle; providing and adjustably coupling an implement to a distal end of the handle such that the implement is disposed at a proximal end of the frame; locating the implement adjacent to a juncture of the frame and the handle such that the implement linearly protrudes outwardly from the handle along the centrally registered longitudinal axis; and the implement removing an existing back liner of an existing medicated patch during an application process of the existing medicated patch.

There has thus been outlined, rather broadly, the more important features of non-limiting exemplary embodiment(s) of the present disclosure so that the following detailed description may be better understood, and that the present contribution to the relevant art(s) may be better appreciated. There are additional features of the non-limiting exemplary embodiment(s) of the present disclosure that will be described hereinafter and which will form the subject matter of the claims appended hereto.

BRIEF DESCRIPTION OF THE NON-LIMITING EXEMPLARY DRAWINGS

The novel features believed to be characteristic of non-limiting exemplary embodiment(s) of the present disclosure are set forth with particularity in the appended claims. The non-limiting exemplary embodiment(s) of the present disclosure itself, however, both as to its organization and method of operation, together with further objects and advantages thereof, may best be understood by reference to the following description taken in connection with the accompanying drawings in which:

Figure 1:
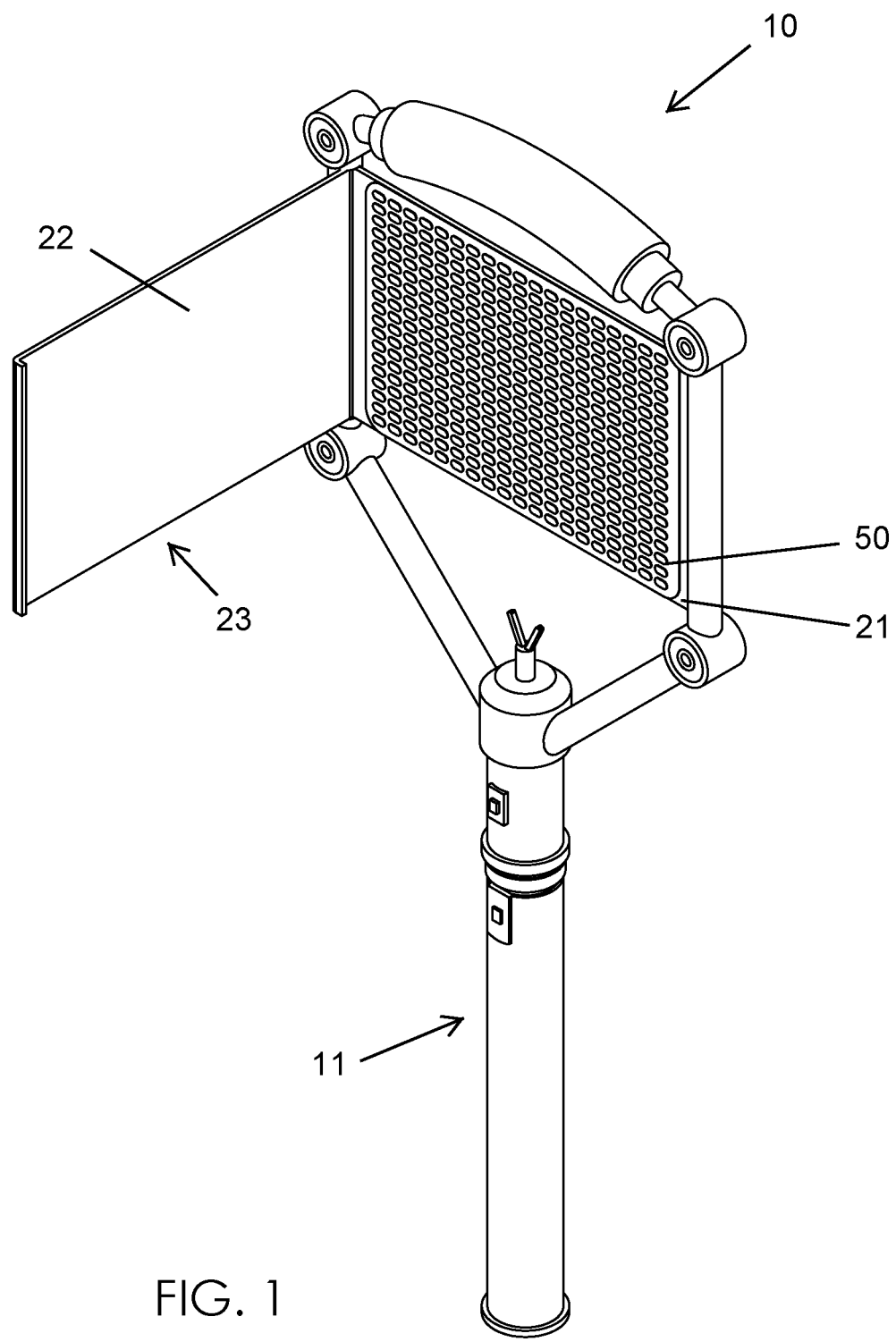
FIG. 1 is a perspective view illustrating a medicated patch applicator having a cover articulated to an open position, in accordance with a non-limiting exemplary embodiment.

Those skilled in the art will appreciate that the figures are not intended to be drawn to any particular scale; nor are the figures intended to illustrate every non-limiting exemplary embodiment(s) of the present disclosure. The present disclosure is not limited to any particular non-limiting exemplary embodiment(s) depicted in the figures nor the shapes, relative sizes or proportions shown in the figures.

DETAILED DESCRIPTION OF NON-LIMITING EXEMPLARY EMBODIMENT(S) OF THE PRESENT DISCLOSURE

The present disclosure will now be described more fully hereinafter with reference to the accompanying drawings, in which non-limiting exemplary embodiment(s) of the present disclosure is shown. The present disclosure may, however, be embodied in many different forms and should not be construed as limited to the non-limiting exemplary embodiment(s) set forth herein. Rather, such non-limiting exemplary embodiment(s) are provided so that this application will be thorough and complete, and will fully convey the true spirit and scope of the present disclosure to those skilled in the relevant art(s). Like numbers refer to like elements throughout the figures.

The illustrations of the non-limiting exemplary embodiment(s) described herein are intended to provide a general understanding of the structure of the present disclosure. The illustrations are not intended to serve as a complete description of all of the elements and features of the structures, systems and/or methods described herein. Other non-limiting exemplary embodiment(s) may be apparent to those of ordinary skill in the relevant art(s) upon reviewing the disclosure. Other non-limiting exemplary embodiment(s) may be utilized and derived from the disclosure such that structural, logical substitutions and changes may be made without departing from the true spirit and scope of the present disclosure. Additionally, the illustrations are merely representational are to be regarded as illustrative rather than restrictive.

One or more embodiment(s) of the disclosure may be referred to herein, individually and/or collectively, by the term "non-limiting exemplary embodiment(s)" merely for convenience and without intending to voluntarily limit the true spirit and scope of this application to any particular non-limiting exemplary embodiment(s) or inventive concept. Moreover, although specific embodiment(s) have been illustrated and described herein, it should be appreciated that any subsequent arrangement designed to achieve the same or similar purpose may be substituted for the specific embodiment(s) shown. This disclosure is intended to cover any and all subsequent adaptations or variations of other embodiment(s). Combinations of the above embodiment(s), and other embodiment(s) not specifically described herein, will be apparent to those of skill in the relevant art(s) upon reviewing the description.

References in the specification to "one embodiment(s)", "an embodiment(s)", "a preferred embodiment(s)", "an alternative embodiment(s)" and similar phrases mean that a particular feature, structure, or characteristic described in connection with the embodiment(s) is included in at least an embodiment(s) of the non-limiting exemplary embodiment(s). The appearances of the phrase "non-limiting exemplary embodiment" in various places in the specification are not necessarily all meant to refer to the same embodiment(s).

Directional and/or relationary terms such as, but not limited to, left, right, nadir, apex, top, bottom, vertical, horizontal, back, front and lateral are relative to each other and are dependent on the specific orientation of an applicable element or article, and are used accordingly to aid in the description of the various embodiment(s) and are not necessarily intended to be construed as limiting.

If used herein, "about" means approximately or nearly and in the context of a numerical value or range set forth means ±15% of the numerical.

If used herein, "substantially" means largely if not wholly that which is specified but so close that the difference is insignificant.

Figure 2:
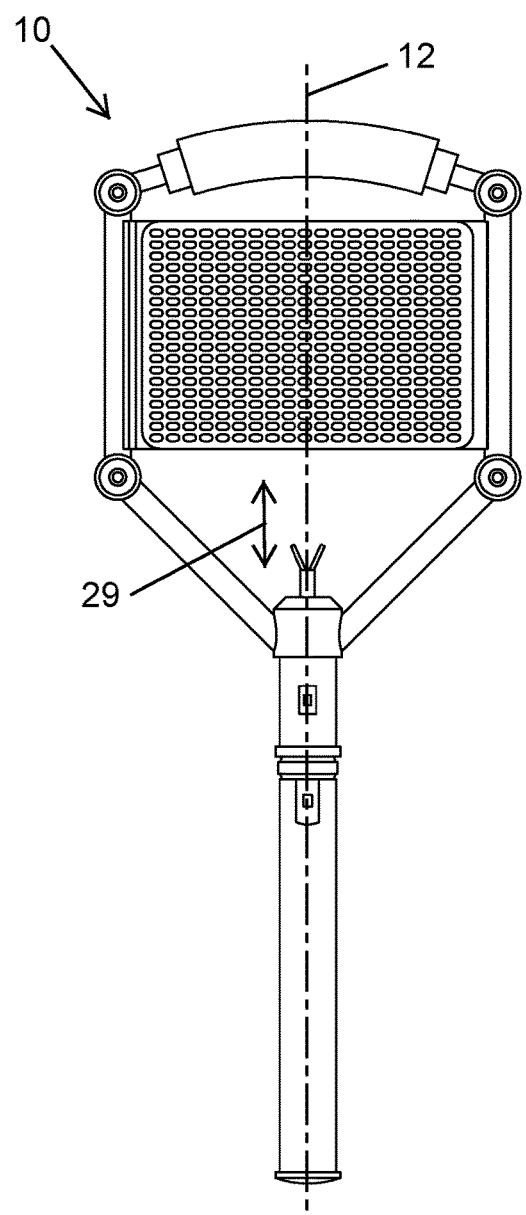
FIG. 2 is a front elevational view of the medicated patch applicator shown in FIG. 1.
Figure 3:
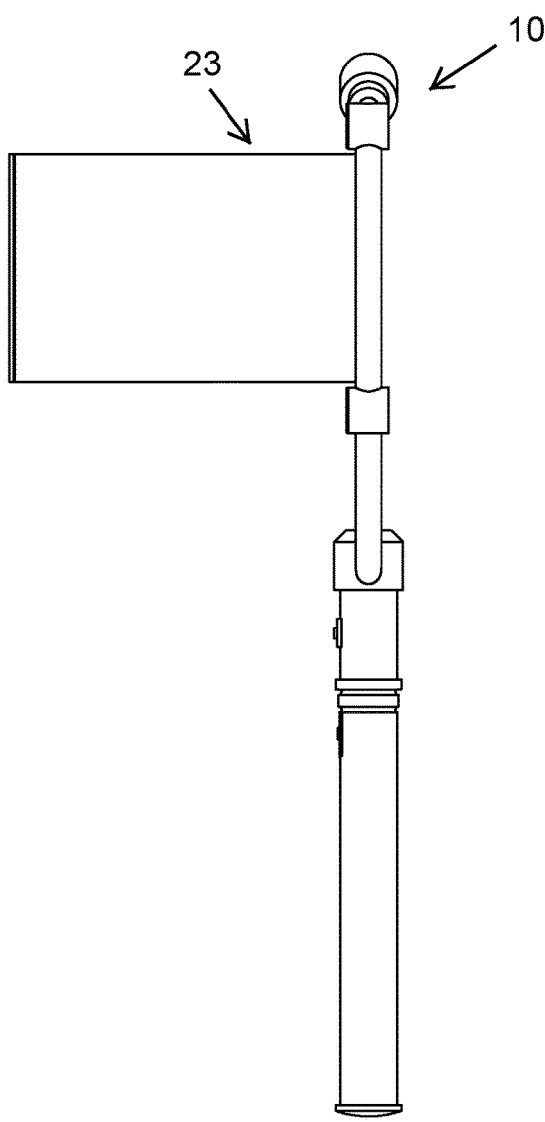
FIG. 3 is a side elevational view of the medicated patch applicator shown in FIG. 1.
Figure 4:
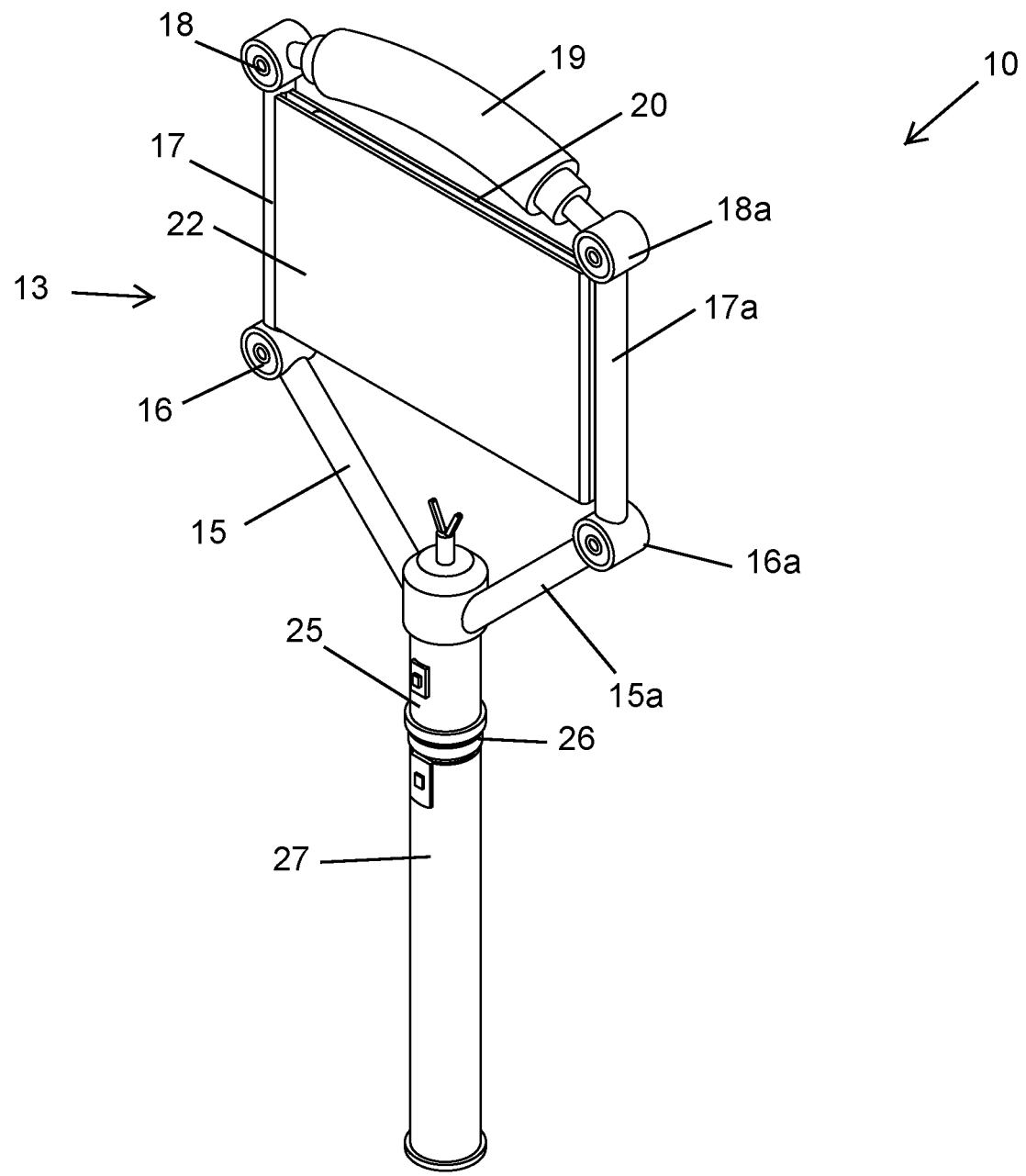
FIG. 4 is a perspective view of the medicated patch applicator shown in FIG. 1, wherein the lid is articulated to a closed position.
Figure 5:
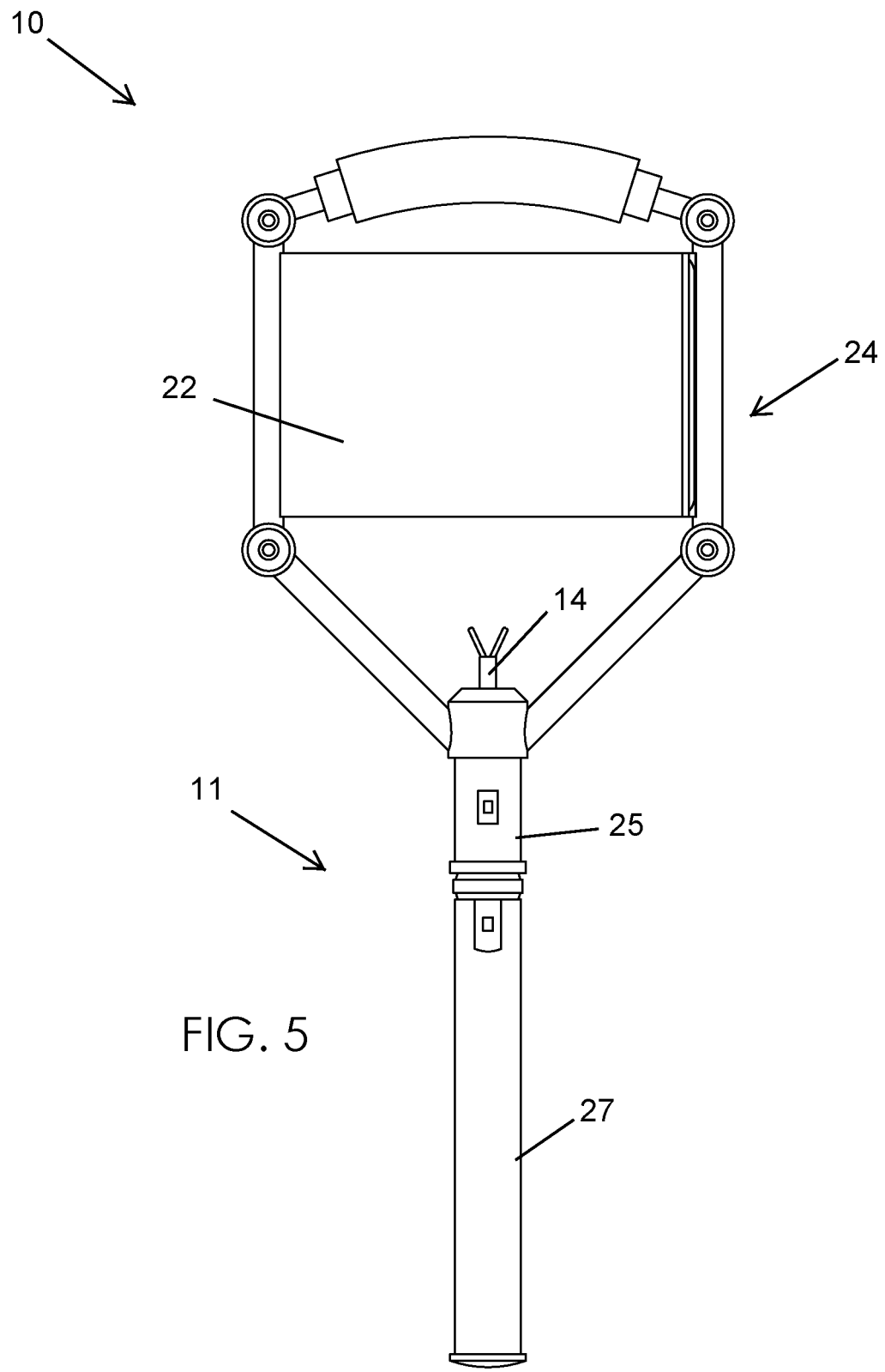
FIG. 5 is a front elevational view of the medicated patch applicator shown in FIG. 4.
Figure 6:
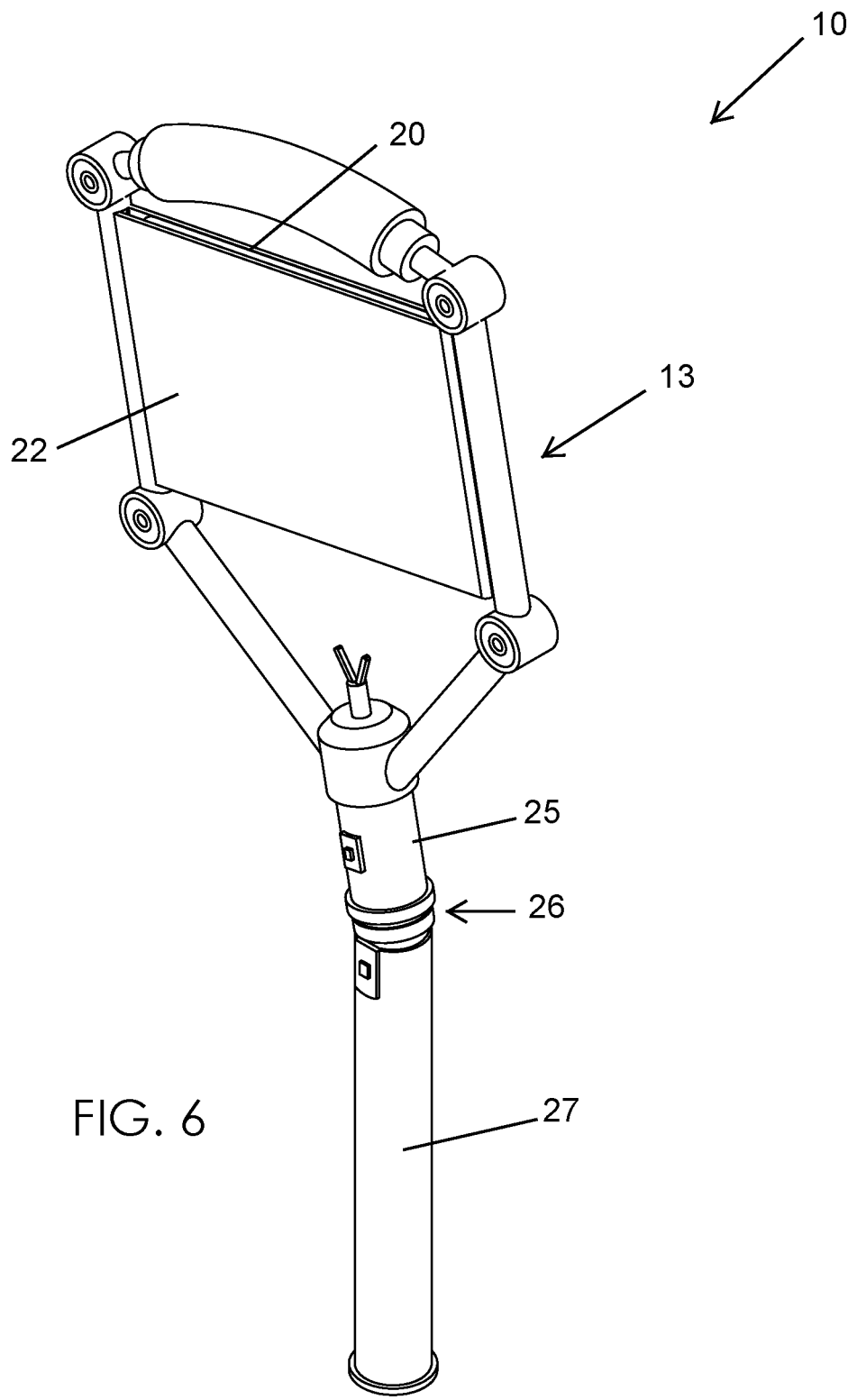
FIG. 6 is a perspective view of the medicated patch applicator shown in FIG. 4, tilted to an angled position.
Figure 7:
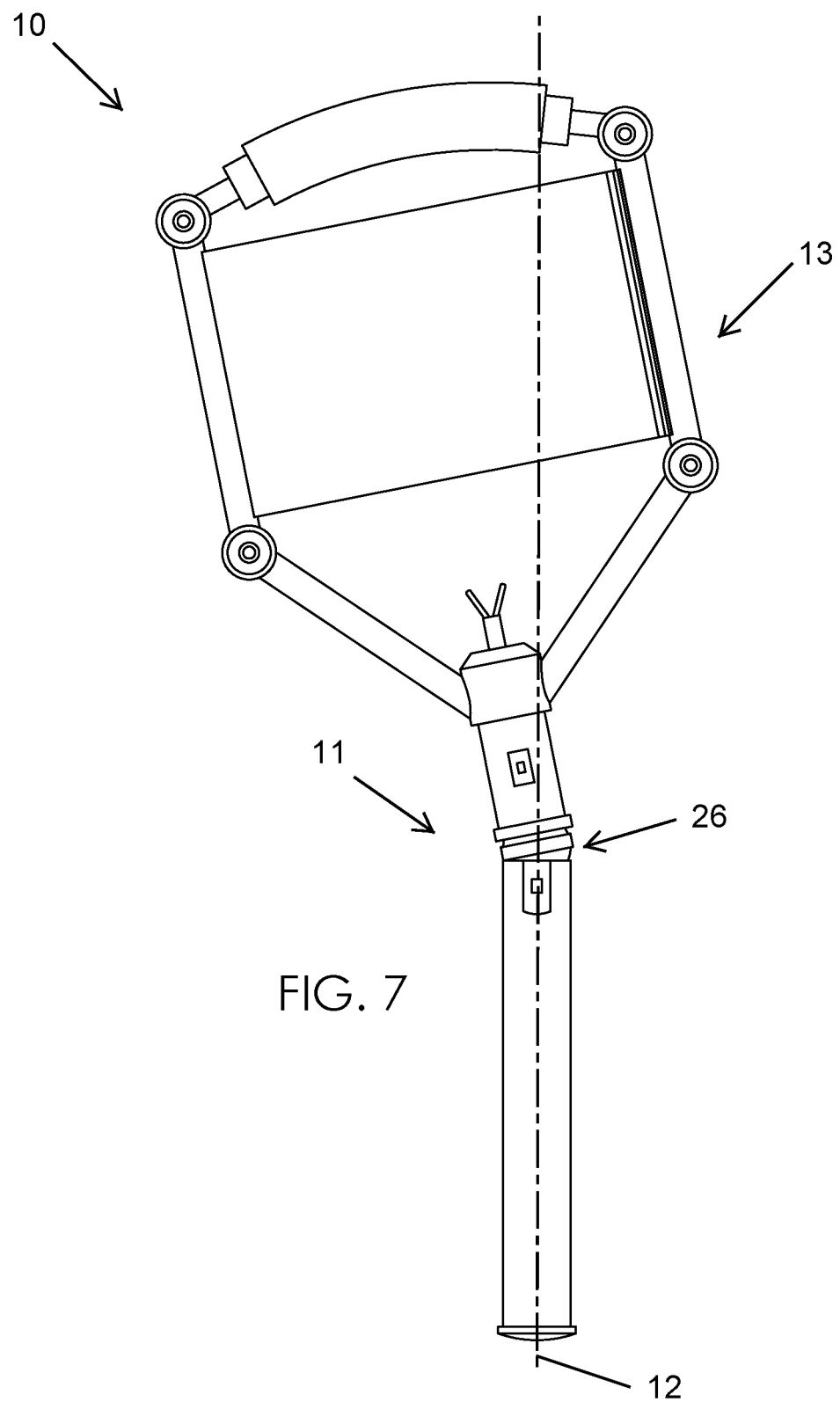
FIG. 7 is a front elevational view of the medicated patch applicator shown in FIG. 6.
Figure 8:
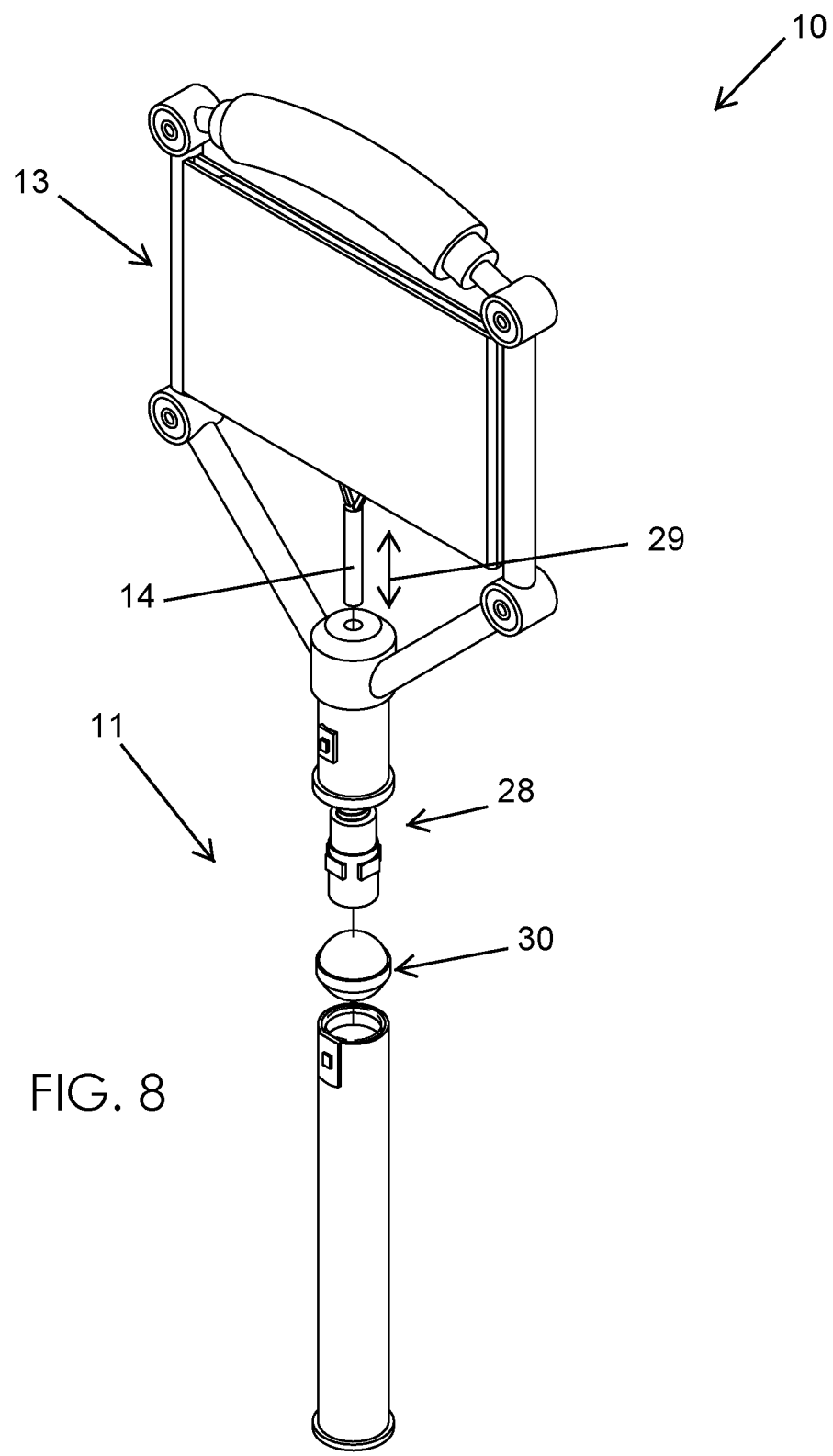
FIG. 8 is an exploded view of the medicated patch applicator shown in FIG. 4.
Figures 9, 9A:
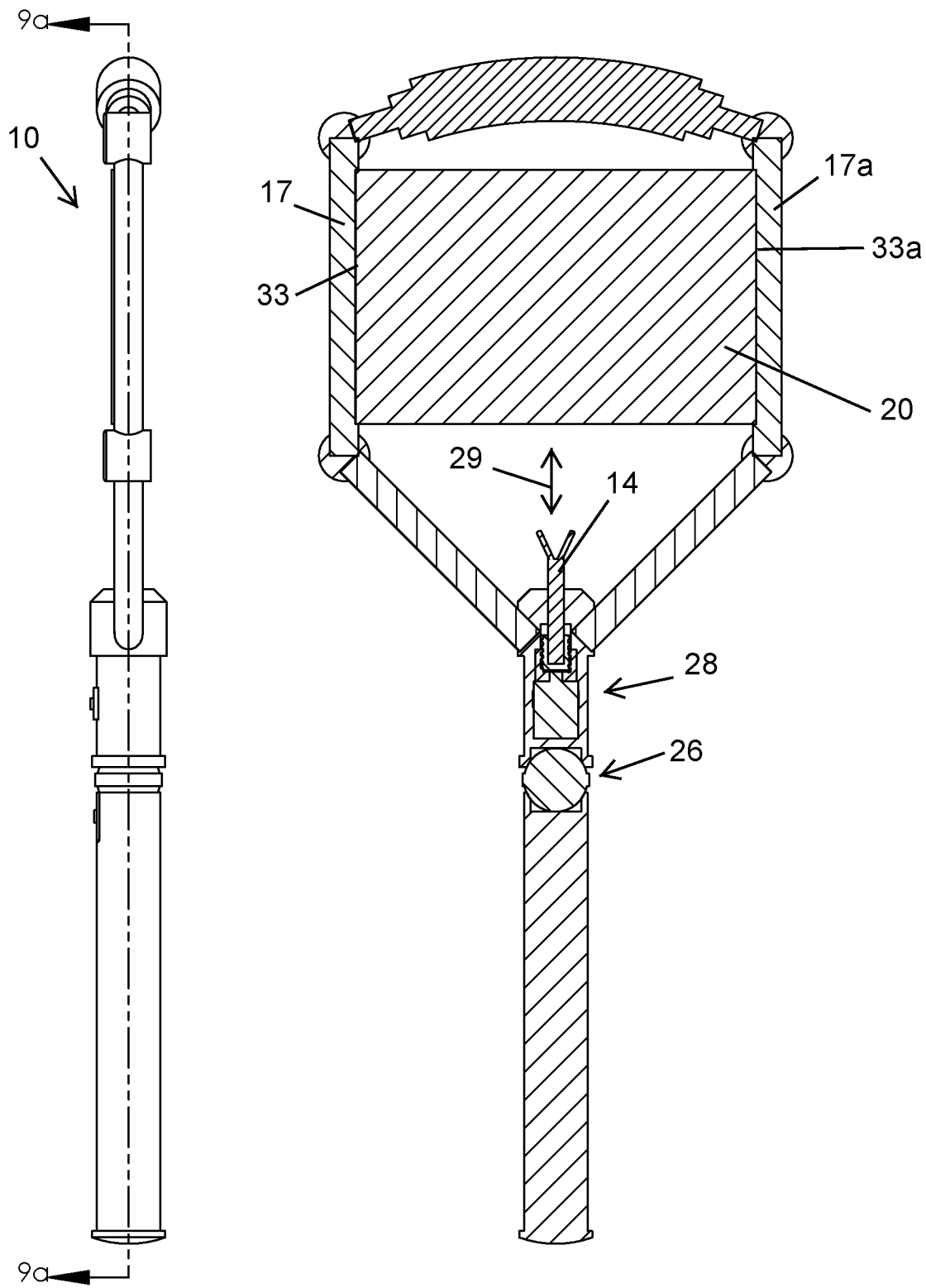
FIG. 9 is a side elevational view of the medicated patch applicator shown in FIG. 4.
FIG. 9a is a cross-sectional view taken along line 9a-9a in FIG. 9.

The non-limiting exemplary embodiment(s) is/are referred to generally in FIGS. 1-9a and is/are intended to provide a medicated patch applicator 10 for easily applying an adhesive-backed, medicated patch to any area of a user back. Such a medicated patch applicator 10 includes a portable handle 11 having a centrally registered longitudinal axis 12, a flexible frame 13 pivotally connected to the handle 11 and selectively articulated relative thereto, and an implement 14 adjustably coupled to a distal end of the handle 11 and disposed at a proximal end of the frame 13. Such an implement 14 is located adjacent to a juncture of the frame 13 and the handle 11 such that the implement 14 linearly protrudes outwardly from the handle 11 along the centrally registered longitudinal axis 12. Advantageously, the implement 14 is capable of removing an existing back liner of an existing medicated patch 50 during an application process of the existing medicated patch 50.

In a non-limiting exemplary embodiment, the frame 13 includes a plurality of flexible struts 15, 15a each having a proximal end coupled to the distal end of the handle 11 and extending outwardly therefrom. Such flexible struts 15, 15a are angularly oriented away from the centrally registered longitudinal axis 12. A plurality of first fasteners 16, 16a are attached to the flexible struts 15, 15a, respectively. A plurality of support arms 17, 17a are attached to the first fasteners 16, 16a and engaged with the flexible struts 15, 15a and extend distally away therefrom, respectively. A plurality of second fasteners 18, 18a are attached to the support arms 17, 17a, respectively, and a roller 19 having axially-offset opposed ends rotatably engaged with the second fasteners 18, 18a, respectively.

In a non-limiting exemplary embodiment, the frame 13 includes a substrate 20 having a planar anterior surface 21 and opposed lateral sides 33, 33a statically mated to the support arms 17, 17a, wherein the substrate 20 is configured to receive the existing medicated patch 50 along the planar anterior surface 21. A cover 22 is pivotally connected to one of the support arms 17, 17a such the cover 22 is articulated between open and closed positions 23, 24 relative to the substrate 20.

In a non-limiting exemplary embodiment, the frame 13 has a substantially Y-shaped configuration.

In a non-limiting exemplary embodiment, the frame 13 has a substantially yoke-shaped configuration.

In a non-limiting exemplary embodiment, the handle 11 includes a first tubular section 25, a pivoting joint 26 disposed at a distal end of the first tubular section 25, and a second tubular section 27 engaged with the pivoting joint 26 and selectively rotatable relative to the first tubular section 25.

In a non-limiting exemplary embodiment, the second tubular section 27 includes an actuator 28 operably coupled to the implement 14 wherein the implement 14 is displaced along a linear path 29 parallel to the centrally registered longitudinal axis 12 when the actuator 28 is depressed.

In a non-limiting exemplary embodiment, the pivoting joint 26 includes a ball and socket mechanism 30 intercalated between the first tubular section 25 and the second tubular section 27.

The present disclosure further includes a method of utilizing a medicated patch applicator 10 for easily applying an adhesive-backed, medicated patch to any area of a user back. Such a method includes the steps of: providing an existing medicated patch 50; providing a portable handle 11 having a centrally registered longitudinal axis 12; providing and pivotally connecting a flexible frame 13 to the handle 11 such that the flexible frame 13 is selectively articulated relative to the handle 11; providing and adjustably coupling an implement 14 to a distal end of the handle 11 such that the implement 14 is disposed at a proximal end of the frame 13; locating the implement 14 adjacent to a juncture of the frame 13 and the handle 11 such that the implement 14 linearly protrudes outwardly from the handle 11 along the centrally registered longitudinal axis 12; and the implement 14 removing an existing back liner of an existing medicated patch 50 during an application process of the existing medicated patch.

A non-limiting exemplary embodiment(s) of the present disclosure is referred to generally in FIGS. 1-9a and is intended to provide a manually operated, handheld device which enables an individual to easily apply an adhesive-backed, medicated patch to any area of his or her back. Ideal for consumers suffering back pain and living alone, the medicated patch applicator 10 permits its users to gain relief from pain, and do so without any assistance to apply the medicated patch. It should be understood that the exemplary embodiment(s) may be used to apply a variety of medicated patches, and should not be limited to any particular medicated patch described herein.

Referring to the figures in general, in a non-limiting exemplary embodiment(s), the medicated patch applicator 10 is handheld and manually operated with which an individual user could reach any area of his or her back, and apply an adhesive-backed medicated patch.

The medicated patch applicator 10 may be fabricated in injection-molded thermoplastic, and includes an adjustable, angled handle 11 and an extended frame 13, at the distal end of which is a rubber roller 19. The handle 11 measures approximately 16 centimeters (cm) in length and 3 to 5 cm in diameter, and features a locking, pivoting joint 26, permitting the handle 11 to meet the top of the frame 13 at an angle of between 120 and 135 degrees. This angle allows the frame 13 and roller 19 of the medicated patch applicator 10 to extend well down (and across, as the case may be) the user's back, while the handle 11—which is finished with an ergonomic, contoured rubber grip—puts no strain on the user's arm or shoulder joint.

From the articulating joint at which the handle 11 meets the frame 13, the medicated patch applicator 10 extends down and out, yoke-like, in the manner of an elongated, inverted "Y". This section, approximately 25 cm in length and 15 cm in width, has a substrate 20 and a cover pivotally coupled thereto. The substrate 20 is suitably sized and shaped to receive the medicated patch. The frame 13 has a pair of semi-flexible struts 15, 15a that angle diagonally inward and support a horizontal shaft or axle on which the rubber roller 19—which might vary in length from 8 to 14 cm—turns. The medicated patch applicator 10 also features a spring-clip, situated at the distal tip of the handle 11, to which the medicated patch 50 liner or backing can be engaged. With the lid at the open position, the medicated patch applicator 10 is rolled down or across the user's back, such that the clip (implement 14) peels away the backing from underneath the patch as the rubber roller—traveling behind the clip on the top surface of the patch—applies the patch smoothly and evenly.

The medicated patch applicator 10 provides a "helping hand" when it comes to relieving an aching, strained back—a helping hand that could easily reach the affected area (without further strain), and smoothly apply a medicated, peel-and-stick patch. While conceived and designed primarily for use by persons living on their own, the medicated patch applicator 10 could be used to advantage by virtually any consumer seeking to alleviate back pain with a patch—business travelers away from home; athletes on road-trips; campers and backpackers; boaters, anglers, and hunters, to name but a few.

While non-limiting exemplary embodiment(s) has/have been described with respect to certain specific embodiment(s), it will be appreciated that many modifications and changes may be made by those of ordinary skill in the relevant art(s) without departing from the true spirit and scope of the present disclosure. It is intended, therefore, by the appended claims to cover all such modifications and changes that fall within the true spirit and scope of the present disclosure. In particular, with respect to the above description, it is to be realized that the optimum dimensional relationships for the parts of the non-limiting exemplary embodiment(s) may include variations in size, materials, shape, form, function and manner of operation.

The Abstract of the Disclosure is provided to comply with 37 C.F.R. § 1.72(b) and is submitted with the understanding that it will not be used to interpret or limit the scope or meaning of the claims. In addition, in the above Detailed Description, various features may have been grouped together or described in a single embodiment for the purpose of streamlining the disclosure. This disclosure is not to be interpreted as reflecting an intention that the claimed embodiment(s) require more features than are expressly recited in each claim. Rather, as the following claims reflect, inventive subject matter may be directed to less than all of the features of any of the disclosed non-limiting exemplary embodiment(s). Thus, the following claims are incorporated into the Detailed Description, with each claim standing on its own as defining separately claimed subject matter.

The above disclosed subject matter is to be considered illustrative, and not restrictive, and the appended claims are intended to cover all such modifications, enhancements, and other embodiment(s) which fall within the true spirit and scope of the present disclosure. Thus, to the maximum extent allowed by law, the scope of the present disclosure is to be determined by the broadest permissible interpretation of the following claims and their equivalents, and shall not be restricted or limited by the above detailed description.

What is claimed as new and what is desired to secure by Letters Patent of the United States is:

1. A medicated patch applicator for easily applying an adhesive-backed, medicated patch to any area of a user back, said medicated patch applicator comprising:
   a handle having a centrally registered longitudinal axis;
   a frame adjustably connected to said handle and selectively articulated relative thereto; and
   an implement coupled to a distal end of said handle and disposed at a proximal end of said frame, said implement being located adjacent to a juncture of said frame and said handle such that said implement linearly protrudes outwardly from said handle along the centrally registered longitudinal axis;
   wherein said implement is capable of removing an existing back liner of an existing medicated patch during an application process of the existing medicated patch.

2. The medicated patch applicator of claim 1, wherein said frame comprises:
   a plurality of flexible struts each having a proximal end coupled to the distal end of said handle and extending outwardly therefrom, said flexible struts being angularly oriented away from the centrally registered longitudinal axis;
   a plurality of first fasteners attached to said flexible struts, respectively;
   a plurality of support arms attached to said first fasteners and engaged with said flexible struts and extending distally away therefrom, respectively;
   a plurality of second fasteners attached to said support arms, respectively; and
   a roller having axially-offset opposed ends rotatably engaged with said second fasteners, respectively.

3. The medicated patch applicator of claim 2, wherein said frame comprises:
   a substrate having a planar anterior surface and opposed lateral sides statically mated to said support arms, wherein said substrate is configured to receive the existing medicated patch along said planar anterior surface; and
   a cover pivotally connected to one of said support arms, said cover being articulated between open and closed positions relative to said substrate.

4. The medicated patch applicator of claim 1, wherein said frame has a substantially Y-shaped configuration.

5. The medicated patch applicator of claim 1, wherein said frame has a substantially yoke-shaped configuration.

6. The medicated patch applicator of claim 1, wherein said handle comprises:
   a first tubular section;
   a pivoting joint disposed at a distal end of said first tubular section; and
   a second tubular section engaged with said pivoting joint and selectively rotatable relative to said first tubular section.

7. The medicated patch applicator of claim 6, wherein said second tubular section comprises:
   an actuator operably coupled to said implement wherein said implement is displaced along a linear path parallel to the centrally registered longitudinal axis when said actuator is depressed.

8. The medicated patch applicator of claim 7, wherein said pivoting joint comprises: a ball and socket mechanism intercalated between said first tubular section and said second tubular section.

9. A medicated patch applicator for easily applying an adhesive-backed, medicated patch to any area of a user back, said medicated patch applicator comprising:
   a portable handle having a centrally registered longitudinal axis;
   a flexible frame pivotally connected to said handle and selectively articulated relative thereto; and
   an implement adjustably coupled to a distal end of said handle and disposed at a proximal end of said frame, said implement being located adjacent to a juncture of said frame and said handle such that said implement linearly protrudes outwardly from said handle along the centrally registered longitudinal axis;
   wherein said implement is capable of removing an existing back liner of an existing medicated patch during an application process of the existing medicated patch.

10. The medicated patch applicator of claim 9, wherein said frame comprises:
   a plurality of flexible struts each having a proximal end coupled to the distal end of said handle and extending outwardly therefrom, said flexible struts being angularly oriented away from the centrally registered longitudinal axis;
   a plurality of first fasteners attached to said flexible struts, respectively;

a plurality of support arms attached to said first fasteners and engaged with said flexible struts and extending distally away therefrom, respectively;

a plurality of second fasteners attached to said support arms, respectively; and a roller having axially-offset opposed ends rotatably engaged with said second fasteners, respectively.

11. The medicated patch applicator of claim 10, wherein said frame comprises:

a substrate having a planar anterior surface and opposed lateral sides statically mated to said support arms, wherein said substrate is configured to receive the existing medicated patch along said planar anterior surface; and a cover pivotally connected to one of said support arms, said cover being articulated between open and closed positions relative to said substrate.

12. The medicated patch applicator of claim 9, wherein said frame has a substantially Y-shaped configuration.

13. The medicated patch applicator of claim 9, wherein said frame has a substantially yoke-shaped configuration.

14. The medicated patch applicator of claim 9, wherein said handle comprises:

a first tubular section;

a pivoting joint disposed at a distal end of said first tubular section; and a second tubular section engaged with said pivoting joint and selectively rotatable relative to said first tubular section.

15. The medicated patch applicator of claim 14, wherein said second tubular section comprises:

an actuator operably coupled to said implement wherein said implement is displaced along a linear path parallel to the centrally registered longitudinal axis when said actuator is depressed.

16. The medicated patch applicator of claim 15, wherein said pivoting joint comprises: a ball and socket mechanism intercalated between said first tubular section and said second tubular section.

17. A method of utilizing a medicated patch applicator for easily applying an adhesive-backed, medicated patch to any area of a user back, said method comprising the steps of:

providing an existing medicated patch;

providing a portable handle having a centrally registered longitudinal axis;

providing and pivotally connecting a flexible frame to said handle such that said flexible frame is selectively articulated relative to said handle;

providing and adjustably coupling an implement to a distal end of said handle such that said implement is disposed at a proximal end of said frame;

locating said implement adjacent to a juncture of said frame and said handle such that said implement linearly protrudes outwardly from said handle along the centrally registered longitudinal axis; and said implement removing an existing back liner of an existing medicated patch during an application process of the existing medicated patch.

* * * * *